United States Patent
Flanagan

(10) Patent No.: US 6,659,769 B2
(45) Date of Patent: Dec. 9, 2003

(54) CORTICAL BONE SPREADER FOR IMPLANTS

(76) Inventor: Dennis Flanagan, 205 Pleasant Valley Rd., Mansfield, CT (US) 06250

( * ) Notice: Subject to any disclaimer, the term of this patent is extended or adjusted under 35 U.S.C. 154(b) by 80 days.

(21) Appl. No.: 10/056,649

(22) Filed: Jan. 25, 2002

(65) Prior Publication Data

US 2003/0143513 A1 Jul. 31, 2003

(51) Int. Cl.$^7$ ................................................. A61C 3/02
(52) U.S. Cl. ........................ 433/144; 433/173; 606/79
(58) Field of Search ................................. 433/144, 141, 433/173, 176; 606/79, 84, 85

(56) References Cited

U.S. PATENT DOCUMENTS

| | | | |
|---|---|---|---|
| 1,598,458 A | | 8/1926 | Sullivan |
| 2,465,305 A | | 3/1949 | Cope |
| 4,553,939 A | * | 11/1985 | Roberts ........................ 433/144 |
| 4,631,030 A | | 12/1986 | von Weissenfluh |
| 4,696,646 A | | 9/1987 | Maitland |
| 4,881,534 A | | 11/1989 | Uhl et al. |
| 5,123,842 A | * | 6/1992 | Roberts ........................ 433/173 |
| 5,217,371 A | | 6/1993 | Lukase et al. |
| 5,743,738 A | | 4/1998 | Baffelli et al. |
| 6,030,390 A | | 2/2000 | Mehdizadeh |
| 6,079,978 A | | 6/2000 | Kunkel |
| 6,110,175 A | * | 8/2000 | Scholl ........................ 606/79 |
| 6,146,138 A | | 11/2000 | Dalmau |
| D439,667 S | | 3/2001 | Brown |

FOREIGN PATENT DOCUMENTS

DE 19732983 * 2/1999

* cited by examiner

Primary Examiner—John J. Wilson
(74) Attorney, Agent, or Firm—Ira S. Dorman

(57) ABSTRACT

A bone spreader for preparing a site for dental prosthesis implantation consists of a relatively flat, wide, blade component and a longitudinal ridge component centrally disposed on one side of the blade component. Penetration of the instrument effects spreading of cortical bone tissue and produces a recess that includes a groove portion within which the root element of a dental implant can be accommodated.

24 Claims, 2 Drawing Sheets

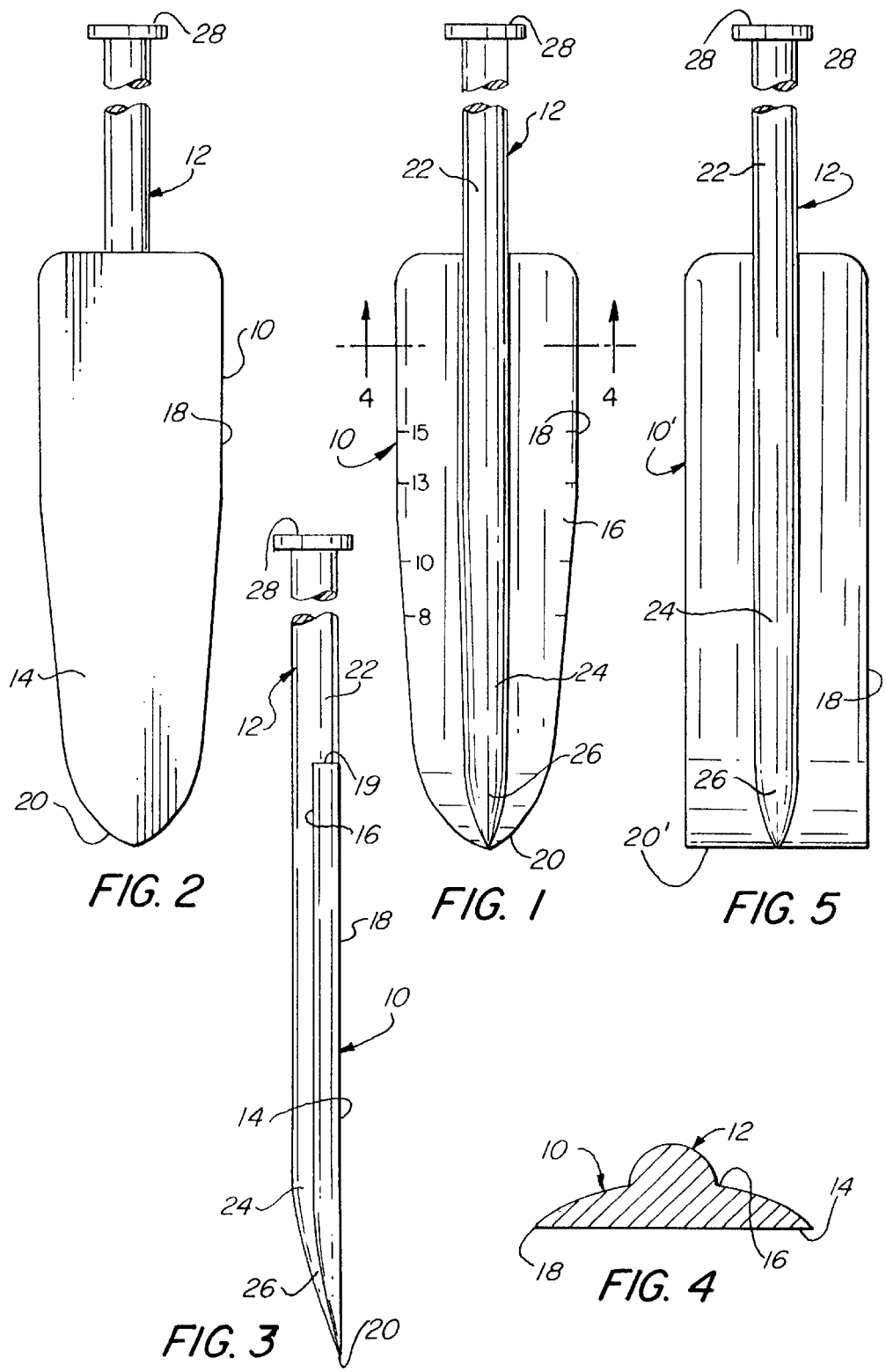

United States Patent 6,659,769 B2

CORTICAL BONE SPREADER FOR IMPLANTS

BACKGROUND OF THE INVENTION

Difficulties are often encountered in the implantation into bone of various prostheses, such as dental implants. Techniques currently employed can contribute to slow healing and less than optimal integration of the implant, and may in some cases lead to excessive bone fracture. Such difficulties are particularly common and/or acute when the site is at a narrow, atrophic bone ridge.

Various dental wedges and like devices are known in the art, as evidenced by the disclosures of the following United States patents:

No. 1,598,458 No. 5,743,738
No. 2,465,305 No. 6,030,390
No. 4,631,030 No. 6,079,978
No. 4,696,646 No. 6,146,138
No. 4,881,534 Des. 439,667
No. 5,217,371

These patents do not however adequately address difficulties and deficiencies that are inherent in conventional implantation practices presently employed.

SUMMARY OF THE INVENTION

The broad objects of the present invention are to provide a novel bone spreader, and a novel method for implant insertion, by which the difficulties and deficiencies described above are avoided, or at least ameliorated, and by which advantages hereinafter set forth are realized.

It has now been found that certain of the foregoing and related objects of the invention are attained by the provision of an instrument having a forward end portion constructed for bone penetration and terminating at a tip, and a rearward end portion constructed for receiving driving force. The instrument is comprised of a relatively wide and thin blade component, which has a relatively sharp peripheral edge portion that extends effectively about at least its forward end portion and that includes laterally spaced edge sections, and an integral ridge component. The ridge component extends rearwardly from adjacent the tip, on one surface of the blade component, and a leading end element thereof, disposed at or closely adjacent the tip, is formed to facilitate bone penetration.

In more specific forms of the instrument, at least a forward end portion of the ridge component will desirably be of substantially curvilinear cross section, and more particularly of half-round form. The forward end portion of the ridge component will usually be tapered, in its lateral and/or its transverse dimensions, so as to provide the penetrating leading end element. The rearward end portion of the instrument will conveniently be provided at least in part by the ridge component, which will normally be substantially rectilinear and disposed intermediate the lateral edge sections of the blade component; generally, the blade component will be laterally symmetric about a central axis on which the ridge component is disposed. One surface of the blade component will beneficially have a generally convex contour, taken in planes transverse to the ridge component along at least a portion of the length of the instrument, and most preferably the blade component will be of generally plano-convex cross section. The blade component will advantageously be gently pointed or will be formed with a rectilinear edge section at the tip of the instrument, and usually the instrument will be integrally formed from a single piece of stainless steel.

Other objects of the invention are attained by the provision of a method for implant insertion, comprising the steps: (a) identifying an implantation site on the surface of a bone member; (b) driving the described bone-spreading instrument so as to spread bone tissue and thereby form an inwardly-extending recess at the implantation site, the recess being dimensioned and configured for the ready receipt of an implant element; (c) removing the instrument from the recess; and (d) inserting the implant element. Normally, the construction of the instrument will be such that a groove of generally semicircular cross section is formed to extend inwardly along one side of the recess, to optimally accommodate a conventional dental implant having a cylindrical root element, with the recess preferably comprising an inwardly tapered plane portion, of relatively wide, thin cross section, and a relatively narrow groove portion extending longitudinally along one side of the plane portion. Depending upon the hardness of the bone at the implantation site, the method may include a preliminary step of forming a pilot slot for receiving the spreader instrument.

BRIEF DESCRIPTION OF THE DRAWINGS

FIG. 1 is a front elevational view, partially broken away, of a cortical bone spreader embodying the present invention;

FIG. 2 is a rear view of the instrument of FIG. 1;

FIG. 3 is a side elevational view of the instrument, as viewed from the right in FIG. 1 (the opposite side view being a virtual mirror image);

FIG. 4 is a transverse sectional view of the instrument, taken along line 4—4 of FIG. 1;

FIG. 5 is a front elevational view, similar to FIG. 1, showing a slightly modified form of the bone spreader;

DETAILED DESCRIPTION OF THE PREFERRED AND ILLUSTRATED EMBODIMENTS

Figure 6A:
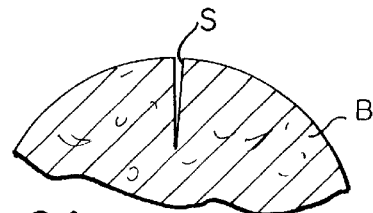
FIGS. 6A–6D are diagrammatic views illustrating the steps of the procedure utilized for producing an implant-receiving recess at a jawbone site, using a spreader embodying the invention.
Figure 6B:
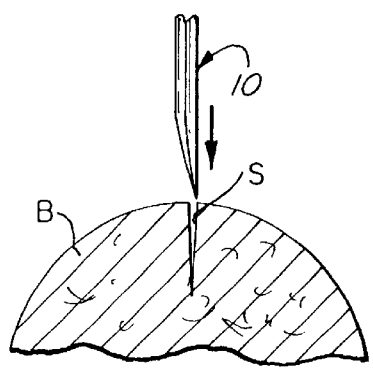

Turning now in detail to FIGS. 1 through 4 of the appended drawings, therein illustrated is a bone spreader embodying the present invention and suitable for use for preparing a site for implantation of a dental prosthesis. The instrument is of one-piece, integrally formed construction, and consists of a blade component and a ridge component generally designated, respectively, by the numerals 10 and 12. The blade component 10 has a relatively planar rear, or lingual, surface 14, and a front, or buccal, surface 16 that is of arcuate cross section along virtually the entire length of the blade component; the surfaces 14, 16 merge to form a sharp peripheral edge 18 that extends entirely about the component, except for the upper shoulder 19. The blade component 10 tapers, both laterally and also transversely, to form a gently pointed tip portion 20 at the leading end of the instrument.

The ridge component 12 extends centrally of the blade portion 10 along its entire length, which is laterally symmetrical thereabout, and includes a stem section 22 projecting beyond its rearward shoulder 19. A head element 28 is formed on the end of the stem section 22, and serves to better adapt the instrument for receiving blows from a surgical mallet or the like, used for forcing the instrument into the bone being prepared; it also facilitates controlled withdrawal. The most forwardly disposed section 26 of the ridge component 12 tapers relatively sharply and leads to a pointed end at the tip 20 of the instrument, so as to facilitate penetration; as will be noted from FIG. 3, the section 26 tapers in both lateral and also transverse directions. The adjacent section 24 is only slightly tapered, and serves to effect a very gradual compression of the bone tissue as the spreader penetrates to increasing depths.

Although suitable dimensions will be apparent to those skilled in the art, and will vary depending upon the application for which the instrument is intended, for dental implantation purposes a bone spreader made in accordance with the invention will typically be about 6 cm in overall length; it will have a blade component about 20 mm long, 5 mm wide and 1.5 mm thick, and the ridge component will be about 3 mm wide and will add about 1.5 mm to the overall thickness. For sizing purposes it might be noted that the ratio of the widths of the blade and ridge components will typically be about 5:3, and the two components will be of about equal thickness.

FIG. 5 shows a second form of bone spreader made in accordance with the present invention; indeed, it is regarded to constitute a preferred embodiment hereof. The instrument of FIG. 5 differs from that of the preceding figures essentially in that the blade component 10' has parallel (rather than tapered) lateral edges, and in that it terminates in a generally transversely extending rectilinear (rather than gently pointed) edge section 20; like the portion 20, the section 20' is formed to have a sharp edge.

FIGS. 6A–6D of the drawings depict the bone spreader of the invention in use for preparing a site on a jawbone B for insertion of a dental implant. As seen in FIG. 6A, a slot S is initially cut with a scalpel (not illustrated); the spreader of the invention is placed into the slot S, is malleted to depth, and is removed, as depicted sequentially in FIGS. 6B through 6D. The last-mentioned Figure shows the recess R produced and remaining after removal of the instrument; bone tissue defining the pilot slot S has of course been compressed and deepened.

Figure 7:
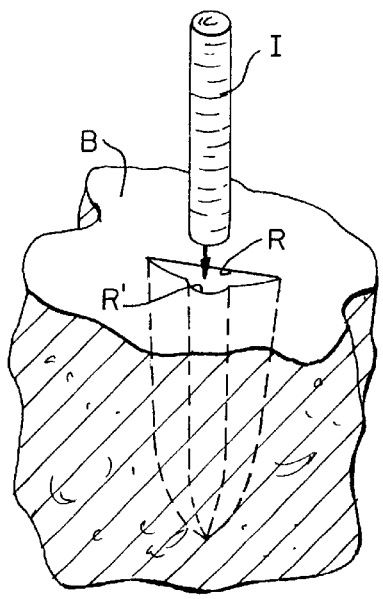
FIG. 7 is an exploded perspective view showing the threaded cylindrical root element of a dental implant positioned for insertion into a site recess made in accordance with the present invention.
Figure 6C:
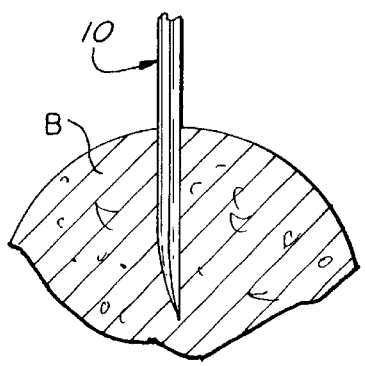
Figure 6D:
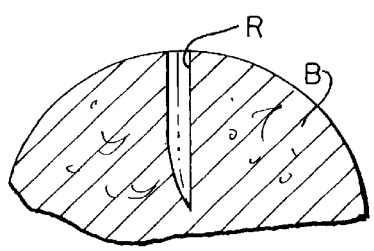
Figure 8:
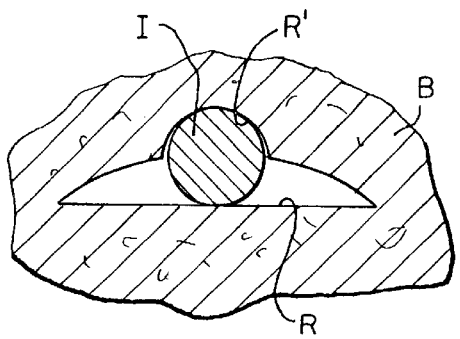
FIG. 8 is a sectional view, drawn to a scale substantially enlarged from that of FIG. 7, showing a root element inserted into a site recess so produced.

The final stage of implant insertion is depicted in FIG. 7, and involves the introduction of the root element of the implant I into the recess R. As can be seen in FIG. 8, the semicylindrical section R', which extends along the relatively thin, wide plane section of the recess, cooperates therewith to receive the implant root element.

It will be appreciated the relatively flat blade portion of the instrument serves to spread cortical bone while the central ridge element further spreads and compresses the bone tissue to open a semicircular channel in which the root element of the implant is readily accepted; the thickness of the blade employed in any given case will be dictated by the amount of interproximal bone available. The tapered construction of the penetrating portions causes a gradual spread of the bone tissue in such a way that stretching is promoted and fracture is minimized. As seen in FIG. 1, a distance scale is advantageously provided on the blade for designating depths of penetration (such as at 8, 10, 13 and 15 mm).

It will also be appreciated that the provision of a generally planar surface on one side of the blade component is important from the standpoint of minimizing distension of bone on that side (the lingual side in a dental application), while accentuating it on the opposite (buccal) side. A similar asymmetric effect is beneficial in other applications for which the spreader of the invention can be employed, such as at intramembranous cranial bone sites.

The procedure for use of the instrument is, as briefly outlined above, simple and straightforward. The site of implantation will initially be inspected and measured for sizing by appropriate conventional means, such as by use of study casts, ridge mapping, palpation, and/or radiologic means. At the beginning of a dental implantation procedure a short envelope-type incision will be made at the crest of the edentulous ridge, the ridge first having been gently and conservatively probed with a dental explorer or periodontal probe under the periosteum, to give the operator a sense of the surface anatomy of the site. The tip of a scalpel (e.g., a #15 scalpel) will then be placed against the crest of the ridge and struck with a surgical mallet so as to penetrate the bone to the hilt of the scalpel, the facial and lingual bone cortices being allowed to guide it into the bone. After removal of the scalpel the tip of the bone spreader will be inserted into the slot produced at the ridge crest, and again a surgical mallet will be used to tap the instrument gently and gradually into the bone so as to cause tissue spreading while, at the same time, minimizing fracture. Penetration is of course made to the appropriate depth for installation of a selected implant, after which the instrument is withdrawn and the implant is immediately placed into the recess produced, in accordance with standard techniques. It is important that the instrument be removed axially, with minimal lateral or rocking motion, to avoid enlargement of the recess. The head element 28 (or similar structure at or near the upper end of the instrument) facilitates such controlled withdrawal, and may serve to engage underlying pliers on the like, which can be tapped in the proper direction to effect removal.

Because the periosteum is not lifted during the procedure it continues to provide a blood supply to the encased bone; this promotes healing at the site and enhances integration of the implant. The elastic nature of the periosteum also permits spreading of the bone, while reenforcing it and containing any fractures that may, nevertheless, occur.

Thus, it can be seen that the present invention provides a novel bone spreader, and a novel method for implant insertion, by which difficulties and deficiencies of current practices are ameliorated or avoided and by which other advantages, hereinabove described, are realized.

Having thus described the invention what is claimed is:

1. An instrument for spreading bone tissue so as to facilitate implant insertion, said instrument having a forward end portion constructed for bone penetration and terminating at a tip, and a rearward end portion constructed for receiving driving force, said instrument being comprised of a relatively wide and thin blade component having a relatively sharp peripheral edge portion, including laterally spaced edge sections and comprising said tip, extending effectively about at least said forward end portion of said instrument, and an integral ridge component extending rearwardly from adjacent said tip on one surface of said blade component, said ridge component having a leading end element, adjacent said tip, that merges with said one surface of said blade component and is formed to facilitate bone penetration.

2. The instrument of claim 1 wherein at least a forward end portion of said ridge component is of substantially curvilinear cross section.

3. The instrument of claim 2 wherein at least said forward end portion of said ridge component is of semicircular cross section.

4. The instrument of claim 2 wherein said forward end portion of said ridge component is tapered, in at least one of its lateral and transverse dimensions, so as to provide said leading end element.

5. The instrument of claim 1 wherein said rearward end portion of said instrument is provided at least in part by said ridge component.

6. The instrument of claim 1 wherein said ridge component is substantially rectilinear.

7. The instrument of claim 6 wherein said blade component is laterally symmetric about a central axis on which said ridge component is disposed.

8. The instrument of claim 1 wherein, taken in planes transverse to said ridge component along at least a portion of the length of said instrument, said one surface of said blade component is convexly curved.

9. The instrument of claim 1 wherein, taken in planes transverse to said ridge component along at least a portion of the length of said instrument, the surface of said blade component opposite to said one surface is substantially planar.

10. The instrument of claim 9 wherein, taken in said transverse planes, said blade component is of generally plano-convex cross section.

11. The instrument of claim 1 wherein said blade component is gently pointed at said tip.

12. The instrument of claim 1 wherein said blade component has a generally transversely extending rectilinear edge section at said tip.

13. The instrument of claim 1 wherein said rearward end portion of said instrument includes head-like structure.

14. In a method for bone implant insertion, the steps comprising:
  (a) identifying an implantation site;
  (b) driving an instrument for spreading bone tissue into bone at said site so as to form a recess extending into said bone, said recess having a portion dimensioned and configured for the ready receipt of an implant element;
  (c) removing said instrument from said recess; and
  (d) inserting an implant element into said recess, said instrument for spreading bone tissue comprising a forward end portion constructed for bone penetration and terminating at a tip, and a rearward end portion constructed for receiving driving force, said instrument being comprised of a relatively wide and thin blade component having a relatively sharp peripheral edge portion, including laterally spaced edge sections and comprising said tip, extending effectively about at least said forward end portion of said instrument, and an integral, relatively narrow ridge component extending rearwardly from adjacent said tip on one surface of said blade component, said ridge component having a leading end element, adjacent said tip, formed to facilitate bone penetration.

15. The method of claim 14 wherein said instrument is constructed for forming a groove of generally semicircular cross section extending inwardly along one side of said recess, and wherein said implant element is generally cylindrical.

16. The method of claim 14 wherein said implant is a dental implant, and wherein said implantation site is at the crest of a jawbone.

17. The method of claim 16 wherein, taken in planes transverse to said ridge component along at least a portion of the length of said instrument, said blade component has a generally planar surface which is disposed to the lingual side in the driven orientation of said instrument.

18. The method of claim 14 including the additional step of forming a pilot slot, at said implantation site, into which said instrument is driven in said step (b).

19. The method of claim 14 wherein said leading end element of said ridge component of said instrument merges with said one surface of said blade component.

20. The method of claim 14 wherein at least a forward end portion of said ridge component of said instrument is of substantially curvilinear cross section.

21. In a method for implant insertion, the steps comprising:
  (a) identifying an implantation site;
  (b) driving an instrument for spreading bone tissue into bone at said site so as to form a recess extending into said bone, said recess being dimensioned and configured for the ready receipt of an implant element;
  (c) removing said instrument from said recess; and
  (d) inserting an implant element into said recess, said recess comprising an inwardly tapered plane portion of relatively wide, thin cross section, and a relatively narrow groove portion extending longitudinally along one side of said plane portion, said groove portion cooperating with said plane portion for receiving said implant element.

22. The method of claim 21 including the additional preliminary step of forming a pilot slot, at said implantation site, into which said instrument is driven in said step (b).

23. The method of claim 21 wherein said instrument is removed essentially axially in said step (c).

24. An instrument for spreading bone tissue so as to facilitate implant insertion, said instrument having a forward end portion constructed for bone penetration and terminating at a tip, and a rearward end portion constructed for receiving driving force, said instrument being comprised of a relatively wide and thin blade component having relatively sharp peripheral edge portion, including laterally spaced edge sections and comprising said tip, extending effectively about at least said forward end portion of said instrument, and an integral ridge component extending rearwardly from adjacent said tip on one surface of said blade component, said ridge component having a leading end element, adjacent said tip, formed to facilitate bone pentration, and at least a forward end portion of said ridge component being of substantially curvilinear cross section.

* * * * *